(12) United States Patent
Cowley (10) Patent No.: US 11,627,981 B2
(45) Date of Patent: Apr. 18, 2023

(54) ULTRASONIC TRANSDUCER ASSEMBLY AND ULTRASONIC SURGICAL INSTRUMENT INCORPORATING THE SAME

(71) Applicant: Covidien LP, Mansfield, MA (US)

(72) Inventor: Matthew S. Cowley, Fredrick, CO (US)

(73) Assignee: Covidien LP, Mansfield, MA (US)

( * ) Notice: Subject to any disclaimer, the term of this patent is extended or adjusted under 35 U.S.C. 154(b) by 258 days.

(21) Appl. No.: 16/722,236

(22) Filed: Dec. 20, 2019

(65) Prior Publication Data
US 2021/0186550 A1   Jun. 24, 2021

(51) Int. Cl.
*A61B 17/32* (2006.01)
*A61B 17/00* (2006.01)
*A61B 17/29* (2006.01)

(52) U.S. Cl.
CPC ............... *A61B 17/320068* (2013.01); *A61B 17/320092* (2013.01); *A61B 2017/00402* (2013.01); *A61B 2017/00734* (2013.01); *A61B 2017/2948* (2013.01); *A61B 2017/320074* (2017.08); *A61B 2017/320089* (2017.08)

(58) Field of Classification Search
CPC ........... A61B 17/320068; A61B 2017/320074; A61B 2017/2948; A61B 17/32092; A61B 2017/32; A61B 2017/09–32009; A61B 2017/320093–320098
USPC ........................................................ 606/169
See application file for complete search history.

(56) References Cited

U.S. PATENT DOCUMENTS

| | | | |
|---|---|---|---|
| 6,063,050 A | | 5/2000 | Manna et al. |
| 6,551,337 B1 | * | 4/2003 | Rabiner ............... A61N 7/022 606/171 |
| 6,786,383 B2 | | 9/2004 | Stegelmann |
| 8,372,101 B2 | | 2/2013 | Smith et al. |
| 8,531,064 B2 | | 9/2013 | Robertson et al. |
| 8,951,272 B2 | | 2/2015 | Robertson et al. |
| 9,326,812 B2 | | 5/2016 | Waaler et al. |
| 2004/0006269 A1 | | 1/2004 | Novak et al. |

(Continued)

FOREIGN PATENT DOCUMENTS

| | | |
|---|---|---|
| AU | 2011323284 A1 | 5/2013 |
| EP | 3520721 A1 | 8/2019 |

OTHER PUBLICATIONS

European Search Report issued in corresponding European Application No. 20214384.8 dated May 18, 2021, 8 pages.

*Primary Examiner* — Kathleen S Holwerda
*Assistant Examiner* — Serenity A Miller
(74) *Attorney, Agent, or Firm* — Carter, DeLuca & Farrell LLP (57) ABSTRACT

An ultrasonic transducer assembly of an ultrasonic surgical instrument includes a piezoelectric stack, an ultrasonic horn secured to and extending distally from the piezoelectric stack and including a body and a nose extending distally from the body, an overmold seal formed about the body of the ultrasonic horn, and a casing disposed about the piezoelectric stack, the body of the ultrasonic horn, and the overmold seal. The casing defines a distal opening through which the nose of the ultrasonic horn extends. The overmold seal establishes a hermetic seal with the casing to define a hermetically sealed interior enclosing the piezoelectric stack and the body of the ultrasonic horn therein.

18 Claims, 4 Drawing Sheets

(56) References Cited

U.S. PATENT DOCUMENTS

| | | |
|---|---|---|
| 2012/0261066 A1 | 10/2012 | Smith et al. |
| 2015/0157354 A1* | 6/2015 | Bales, Jr. ............... A61B 50/20 606/169 |
| 2016/0121143 A1 | 5/2016 | Mumaw et al. |
| 2016/0206900 A1 | 7/2016 | Haberstich et al. |
| 2017/0202595 A1* | 7/2017 | Shelton, IV ....... A61B 18/1445 |
| 2018/0014846 A1* | 1/2018 | Rhee .................... B06B 1/0611 |
| 2018/0014848 A1 | 1/2018 | Messerly et al. |
| 2019/0159793 A1* | 5/2019 | Cotter ................. A61M 1/0058 |

\* cited by examiner

ULTRASONIC TRANSDUCER ASSEMBLY AND ULTRASONIC SURGICAL INSTRUMENT INCORPORATING THE SAME

BACKGROUND

Technical Field

The present disclosure relates to ultrasonic surgical instruments and, more particularly, to an ultrasonic transducer assembly and ultrasonic surgical instrument including the same.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, and/or fulgurate tissue to effect hemostasis.

Ultrasonic surgical instruments typically employ a transducer coupled to a handle of the ultrasonic surgical instrument and configured to produce ultrasonic energy for transmission along a waveguide to an end effector of the ultrasonic surgical instrument that is designed to treat tissue with the ultrasonic energy. The transducer may be driven by an ultrasonic generator that is on-board, e.g., on or within the handle of the ultrasonic surgical instrument, or remotely disposed, e.g., as a set-top box connected to the ultrasonic surgical instrument via a surgical cable. The end effector of the ultrasonic surgical instrument may include a blade that receives the ultrasonic energy from the waveguide for application to tissue and a jaw member configured to clamp tissue between the blade and the jaw member to facilitate treatment thereof.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is an ultrasonic transducer assembly of an ultrasonic surgical instrument. The ultrasonic transducer assembly includes a piezoelectric stack, an ultrasonic horn, an overmold seal, and a casing. The ultrasonic horn is secured to and extends distally from the piezoelectric stack. The ultrasonic horn includes a body and a nose extending distally from the body. The overmold seal is formed about the body of the ultrasonic horn. The casing is disposed about the piezoelectric stack, the body of the ultrasonic horn, and the overmold seal. The casing defines a distal opening through which the nose of the ultrasonic horn extends. The overmold seal establishes a hermetic seal with the casing to define a hermetically sealed interior enclosing the piezoelectric stack and the body of the ultrasonic horn therein.

In an aspect of the present disclosure, the body of the ultrasonic horn is formed from first and second body portions joined to one another at a seam. The first and second body portions may be joined to one another at the seam via welding. Additionally or alternatively, the seam may be disposed near a node location (within 10% of a node location) along the ultrasonic horn. Further, the first and second body portions may include complementary opposing faces to facilitate joining.

In another aspect of the present disclosure, the body of the ultrasonic horn defines an annular recess and the overmold seal is disposed within and about the annular recess. In such aspects, the annular recess of the body of the ultrasonic horn may be discontinuous.

In yet another aspect of the present disclosure, the overmold seal includes at least one pass-through electrical connector extending therethrough. In such aspects, first and second electrode assemblies disposed within the hermetically sealed interior and associated with the piezoelectric stack and electrically coupled to first and second pass-through electrical connectors of the at least one pass-through electrical connector.

In still another aspect of the present disclosure, the casing includes a plurality of casing components joined to one another at hermetically sealed seams.

An ultrasonic surgical instrument provided in accordance with aspects of the present disclosure includes a handle assembly and an elongated assembly. The handle assembly includes a housing and an ultrasonic transducer assembly according to any of the aspects detailed above or otherwise herein. The elongated assembly extends distally from the handle assembly. The elongated assembly includes a waveguide that is configured to engage the nose of the ultrasonic horn and that defines a blade at a distal end thereof. Ultrasonic energy produced by the piezoelectric stack is transmitted along the ultrasonic horn and the waveguide to the blade for treating tissue adjacent the blade.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
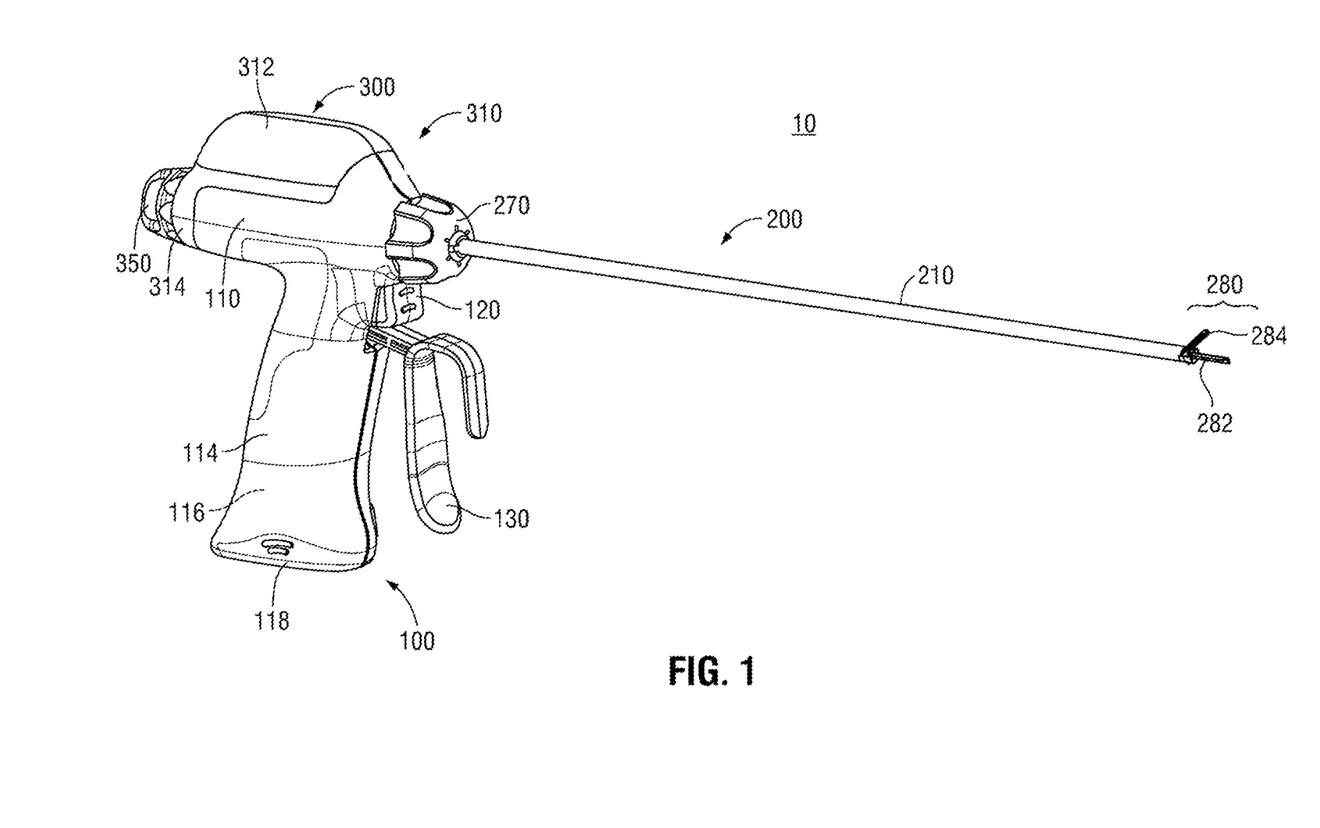
FIG. 1 is a side, perspective view of an ultrasonic surgical instrument provided in accordance with the present disclosure.
Figure 2:
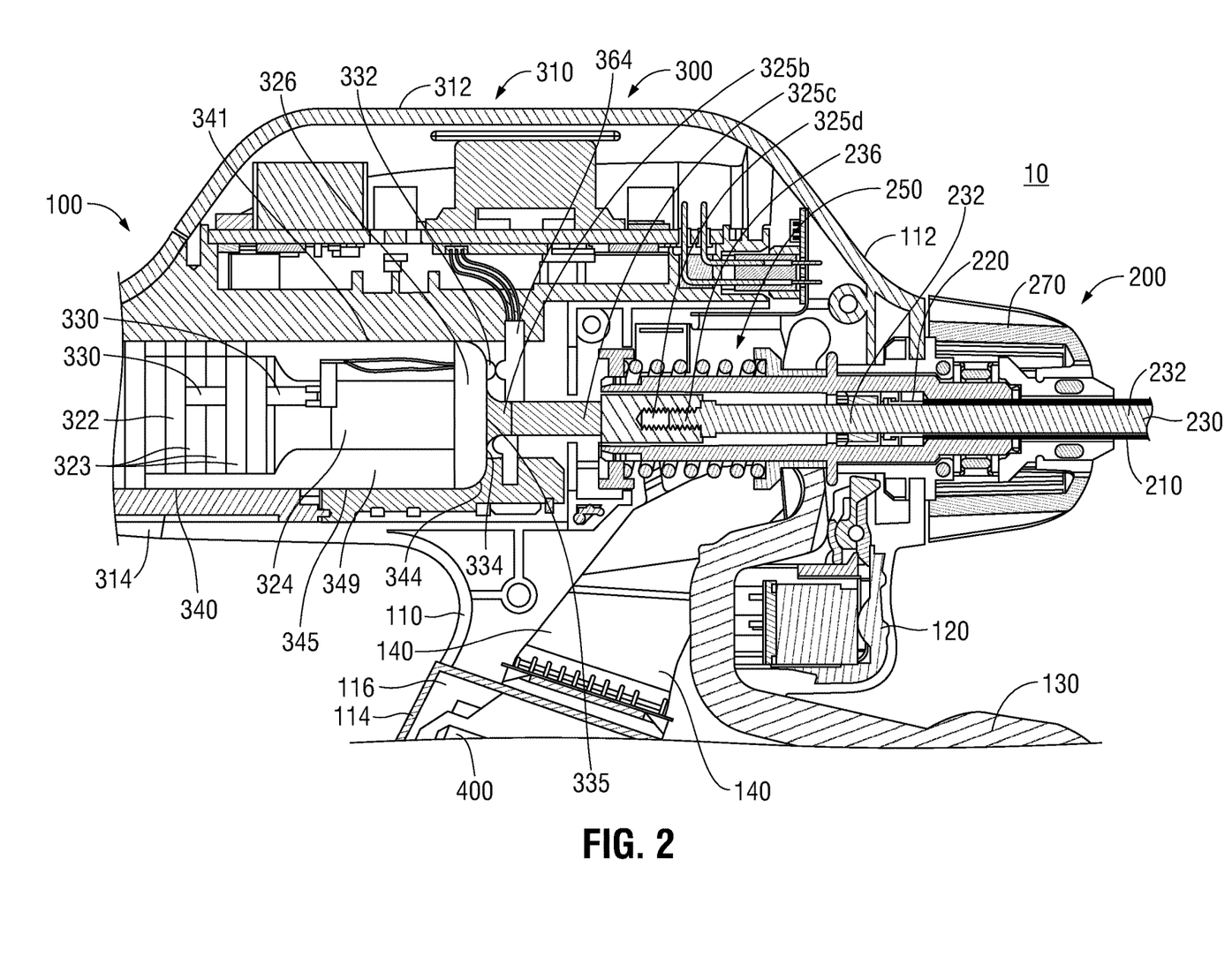
FIG. 2 is an enlarged, side, longitudinal, cross-sectional view of a proximal portion of the ultrasonic surgical instrument of FIG. 1.

Referring to FIGS. 1 and 2, an ultrasonic surgical instrument provided in accordance with the present disclosure is shown generally identified by reference numeral 10. Ultrasonic surgical instrument 10 includes a handle assembly 100 and an elongated assembly 200 extending distally from handle assembly 100. Handle assembly 100 includes a housing 110 defining a body portion 112 and a fixed handle portion 114. Handle assembly 100 further includes an activation button 120 and a clamp trigger 130.

Body portion 112 of housing 110 is configured to support an ultrasonic transducer and generator assembly ("TAG") 300 including a generator assembly 310 and an ultrasonic transducer assembly 320. TAG 300 may be permanently engaged with body portion 112 of housing 110 or removable therefrom. Generator assembly 310 includes a housing 312 configured to house the internal electronics of generator assembly 310, and a cradle 314 configured to rotatably support ultrasonic transducer assembly 320. Alternatively, generator assembly 310 may be remotely disposed and coupled to ultrasonic surgical instrument 10 by way of a surgical cable.

Fixed handle portion 114 of housing 110 defines a compartment 116 configured to receive a battery assembly 400 and a door 118 configured to enclose compartment 116. An electrical connection assembly 140 is disposed within housing 110 of handle assembly 100 and serves to electrically couple activation button 120, generator assembly 310 of TAG 300, and battery assembly 400 with one another when TAG 300 is supported on or in body portion 112 of housing 110 and battery assembly 400 is disposed within compartment 116 of fixed handle portion 114 of housing 110, thus enabling activation of ultrasonic surgical instrument 10 in response to depression of activation button 120. In embodiments where generator assembly 310 is remote from ultrasonic surgical instrument 10, battery assembly 400 and the configuration of fixed handle portion 114 for receiving battery assembly 400 need not be provided, as generator assembly 310 may be powered by a standard wall outlet or other remote power source.

Referring still to FIGS. 1 and 2, elongated assembly 200 of ultrasonic surgical instrument 10 includes an outer drive sleeve 210, an inner support sleeve 220 disposed within outer drive sleeve 210, a waveguide 230 extending through inner support sleeve 220, a drive assembly 250, a rotation knob 270, and an end effector 280 including a blade 282 and a jaw 284. A proximal portion of outer drive sleeve 210 is operably coupled to clamp trigger 130 of handle assembly 100 via drive assembly 250, while a distal portion of outer drive sleeve 210 is operably coupled to jaw 284. As such, clamp trigger 130 is selectively actuatable to thereby move outer drive sleeve 210 about inner support sleeve 220 to pivot jaw 284 relative to blade 282 of end effector 280 from a spaced-apart position to an approximated position for clamping tissue between jaw 284 and blade 282. Drive assembly 250 provides a force-limiting feature whereby the clamping pressure applied to tissue is limited to a particular clamping pressure or particular clamping pressure range. Rotation knob 270 is rotatable in either direction to rotate elongated assembly 200 in either direction relative to handle assembly 100.

Waveguide 230 extends through inner support sleeve 220. Waveguide 230 defines a body 232 and a blade 282 extending from the distal end of body 232. Blade 282 serves as the blade of end effector 280. Waveguide 230 further includes a proximal threaded male connector 236 configured for threaded engagement within threaded female receiver 325d of ultrasonic horn 324 of ultrasonic transducer assembly 320 such that ultrasonic vibrations produced by ultrasonic transducer assembly 320 are transmitted along waveguide 230 to blade 282 for treating tissue clamping between blade 282 and jaw 284 or positioned adjacent to blade 282.

Figure 3:
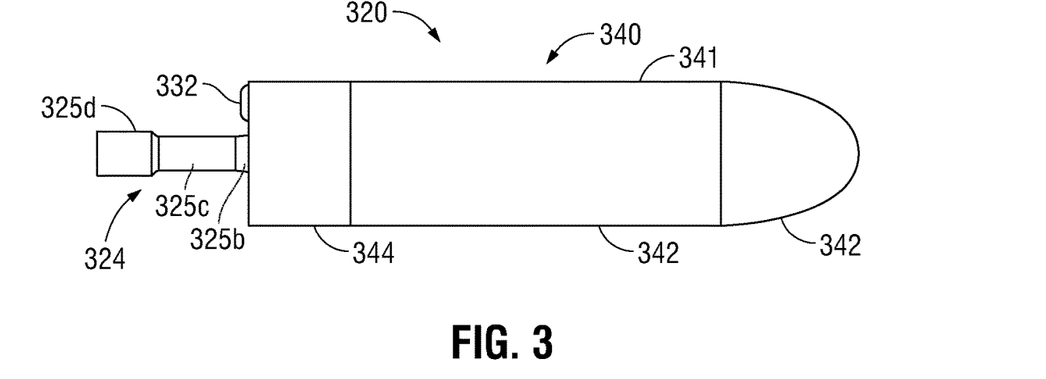
FIG. 3 is an enlarged, side view of the transducer assembly of the ultrasonic surgical instrument of FIG. 1.

Referring to FIGS. 2 and 3, ultrasonic transducer assembly 320 includes a piezoelectric stack 322, an ultrasonic horn 324, an overmold seal 326, a bolt 328 (FIG. 7), a proximal nut 329, first and second electrode assemblies 330, a contact assembly 332, and an outer casing 340. Bolt 328 (FIG. 7) secures piezoelectric stack 322 between ultrasonic horn 324 and proximal nut 329. First and second electrode assemblies 330 are interdisposed between the piezoelectric elements 323 of piezoelectric stack 322 and connect to contact assembly 332. Contact assembly 332 enables communication of drive and/or data signals through outer casing 340, e.g., between piezoelectric stack 322 and/or ultrasonic horn 324 and generator assembly 310.

Outer casing 340 defines a body 341 formed from one or more proximal body components 342 and a distal body component 344 joined to one another via welding or in any other suitable manner that provides hermetically-sealed weld seams. Distal body component 344 defines an aperture 334 therethrough to permit passage of nose 325b of ultrasonic horn 324 therethrough. Overmold seal 326, as detailed below, is formed about body 325a of ultrasonic horn 324 towards the distal end thereof and disposed within outer casing 340 in hermetic sealing relation with an internal annular surface and/or an internal proximally-facing surface of distal body component 344 of body 341 of outer casing 340 to define a hermetically sealed enclosure 345 enclosing an internal volume 349 defined by body 341, overmold seal 326, and ultrasonic horn 324. Enclosure 345 hermetically seals, within internal volume 349, the piezoelectric stack 322, a proximal portion of ultrasonic horn 324, bolt 328, proximal nut 329, and first and second electrode assemblies 330.

A rotation knob 350 (FIG. 1) may be defined, mounted, or coupled to a proximal end portion of outer casing 340. As shown in FIG. 1, rotation knob 350 is accessible from the exterior of handle assembly 100 and is configured for manual rotation to rotate ultrasonic transducer assembly 320 relative to generator assembly 310 and housing 110.

Continuing with reference to FIGS. 2 and 3, generator assembly 310 includes a contact assembly 364 (including a plurality of contacts) disposed in slidable contact with contact assembly 332 (including a plurality of contacts) of ultrasonic transducer assembly 320. Thus, the contacts of contact assembly 364 and the contacts of ultrasonic transducer assembly 320 define slidable contact assemblies e.g., a slip ring contact assembly, that enable drive and/or data signals to be communicated between generator assembly 310 and piezoelectric stack 322 (or other components of) of ultrasonic transducer assembly 320 regardless of the rotational orientation of ultrasonic transducer assembly 320 relative to generator assembly 310.

More specifically, with respect to drive signal communication, the first of the electrode assemblies 330 includes at least one positive electrode disposed between the piezoelectric elements 323 of piezoelectric stack 322 and an electrode connector connecting the at least one positive electrode with one of the contacts of contact assembly 332 which, in turn, is disposed in electrical connection with one of the contacts of contact assembly 364 of generator assembly 310. The second of the electrode assemblies 330 includes at least one negative electrode disposed between the piezoelectric elements 323 of piezoelectric stack 322 and an electrode connector connecting the at least one negative electrode with another one of the contacts of contact assembly 332 which, in turn, is disposed in electrical connection with another of the contacts of contact assembly 364 of generator assembly 310. As such, a drive signal voltage may be applied from generator assembly 310 across the piezoelectric elements 323 of the piezoelectric stack 322 via the positive and negative electrodes. The piezoelectric stack 322, in turn, converts the applied voltage into mechanical energy, in the form of ultrasonic vibrations, that is transmitted to ultrasonic horn 324.

With respect to data signal communication, contact assembly 332 may include a data chip (not explicitly shown) (or electrical connectors, with the data chip disposed within generator assembly 310) disposed in communication with ultrasonic horn 324 (and/or other portions of ultrasonic transducer assembly 320). The data chip, more specifically, may be a microprocessor chip or other suitable chip with sensory circuitry to detect various conditions, parameters, properties, etc. of piezoelectric stack 322, ultrasonic horn 324, and/or other portions of ultrasonic transducer assembly 320. The data chip may be configured to sense, for example, a frequency, amplitude, impedance, and/or temperature of ultrasonic horn 324 (or other portion of ultrasonic transducer assembly 320); the number of times ultrasonic transducer assembly 320 has been activated, the duration of activation ultrasonic transducer assembly 320, etc. The data chip may additionally or alternatively include a memory storing information relating to ultrasonic transducer assembly 320 such as, for example, model, serial number, manufacture date, calibration and/or testing information, manufacturer setting information, etc. In embodiments where the data chip includes sensor circuitry, the memory may also store the sensed data.

The data chip (or electrical connectors) within ultrasonic transducer assembly 320 is coupled to another one of the contacts of contact assembly 332 which, in turn, is disposed in electrical connection with another of the contacts of contact assembly 364 of generator assembly 310 to enable communication of data signals between ultrasonic transducer assembly 320 and ultrasonic generator assembly 310.

Figure 4:
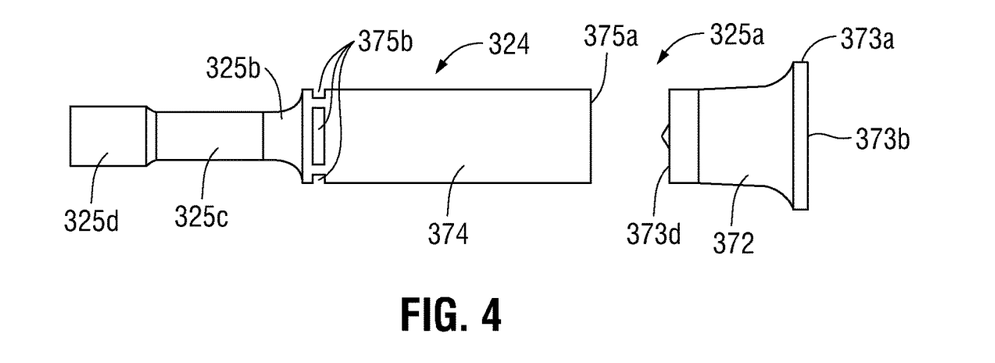
FIG. 4 is an exploded, side view of the ultrasonic horn of the transducer assembly of FIG. 3.

Turning to FIGS. 3-7, and with initial reference to FIG. 4, as mentioned above, ultrasonic horn 324 includes a body 325a and a nose 325b extending distally from body 325a. Body 325a includes a proximal body portion 372 and a distal body portion 374. Distal body portion 374 of body 325a and nose 325b may be formed monolithically from a single piece of material, while proximal body portion 372 is formed separately and subsequently attached to distal body portion 374, e.g., via welding, at a seam to form ultrasonic horn 324, although other configurations are also contemplated.

Proximal body portion 372 defines a flared proximal end 373a defining a proximal face 373b including an aperture 373c defined therethrough. A distal face 373d of proximal body portion 372 and a proximal face 375a of distal body portion 374 may define complementary features, e.g., complementary protrusion(s) and recess(es), to facilitate alignment for attachment, e.g., welding. The joint where distal face 373d of proximal body portion 372 and proximal face 375a of distal body portion 374 are joined may be located at an anti-node point such that no internal stresses are imparted thereto.

Distal body portion 374 of body 325a defines an annular recess 375b towards but spaced-apart from a distal end thereof. Annular recess 375b may be continuous, e.g., extending continuously about the circumference of distal body portion 374, or may be defined by one or more discontinuous recess segments extending about the circumference of distal body portion 374 (as shown).

Nose 325b extends distally from distal body portion 374 of body 325a and tapers from the larger diameter of distal body 374 to a smaller diameter of an extension 325c that extends distally from nose 325b to threaded female receiver 325d. Nose 325b extends through aperture 334 of distal body component 344 of outer casing 340 (see FIG. 2) such that body 325a is disposed within outer casing 340 (FIG. 2) while extension 325c and threaded female receiver 325d are disposed externally of outer casing 340 (FIG. 2).

Figure 5:
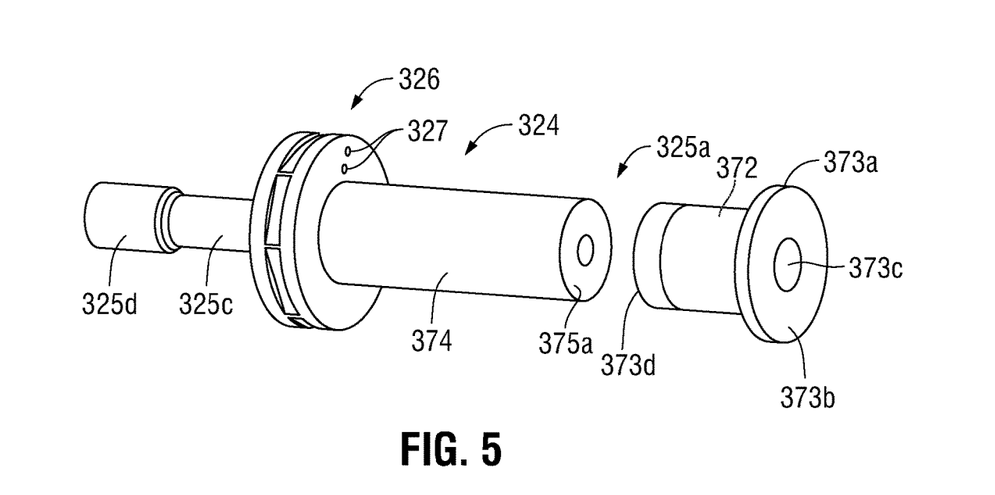
FIG. 5 is an exploded, perspective view of the ultrasonic horn as illustrated in FIG. 4 including an overmolded seal disposed thereon.

With additional reference to FIG. 5, overmold seal 326 is formed from any suitable polymeric material and is overmolded about (and within) annular recess 375b of distal body portion 374 of body 325a of ultrasonic horn 324 to define a donut-shaped seal extending radially outwardly from distal body portion 374 towards the distal end thereof. The overmolding of overmold seal 326 about annular recess 375b of distal body portion 374 forms a hermetic seal between overmold seal 326 and distal body portion 374.

Overmold seal 326, in embodiments, may be formed to include a plurality of pass-through electrical contacts 327 (e.g., pins, rings, or other suitable contacts) extending longitudinally therethrough, e.g., from a distal face to a proximal face thereof, in hermetically sealed relation therewith to enable electrical signals to be communicated across overmold seal 326 without compromising the hermetic seal. In this manner, as shown in FIG. 2, the electrode assemblies 330 disposed within internal volume 349 of hermetically sealed enclosure 345 can electrically couple with the externally-disposed contact assembly 332 via pass-through electrical contacts 327 (see FIG. 2). Data and other signals may additionally or alternatively be communicated between the internal volume 349 of hermetically sealed enclosure 345 and the exterior via pass-through electrical contacts 327 (see FIG. 2). As an alternative or in addition to pass-through contacts 327, overmold seal 326 may include a conductive shell (not shown) to enable electrical communication therethrough and/or communication may otherwise be communicated through outer casing 340.

Figure 6:
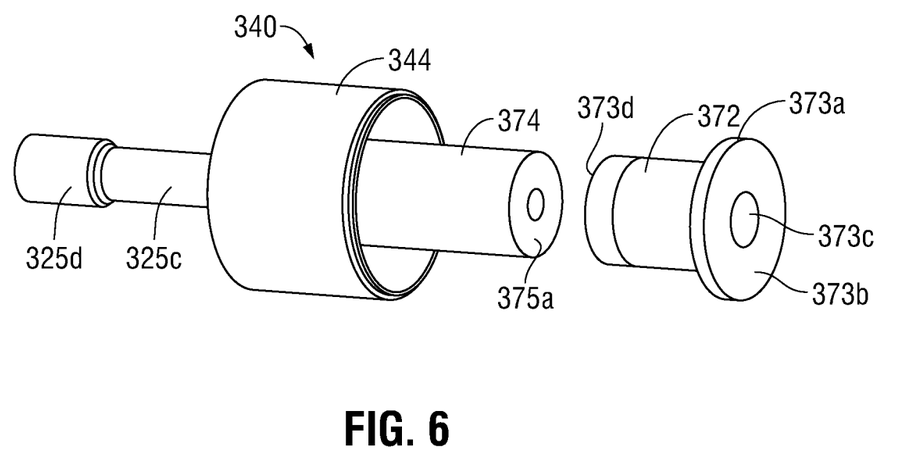
FIG. 6 is an exploded, perspective view of the ultrasonic horn as illustrated in FIG. 5 including a distal component of the outer casing disposed thereon.

Turning to FIG. 6, in conjunction with FIG. 5, overmold seal 326 defines a radial dimension such that an outer annular surface thereof is configured to hermetically seal against an internal annular surface of distal body component 344 of body 341 of outer casing 340. Additionally or alternatively, a distal face of overmold seal 326 is configured to hermetically seal against an internal proximally-facing surface of distal body component 344 of body 341 of outer casing 340. Thus, overmold seal 326 defines the distal end of enclosure 345 (FIG. 2). As detailed below, outer casing 340 defines the proximal end and radial boundaries of enclosure 345 (FIG. 2).

Figure 7:
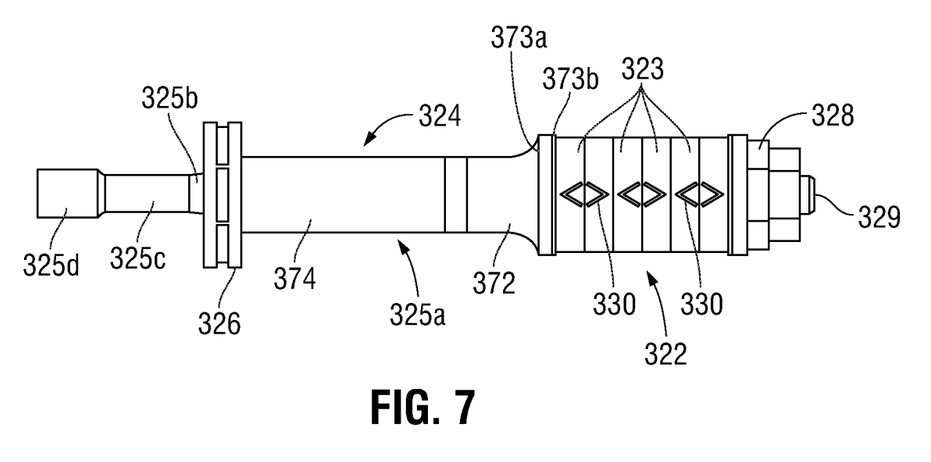
FIG. 7 is a side view of the transducer assembly of FIG. 3 with the outer casing removed.

Referring to FIGS. 5 and 7, once overmold seal 326 is formed about distal body portion 374 of ultrasonic horn 324 (or in any other suitable sequence during manufacturing), distal body portion 374 and proximal body portion 372 may be attached to one another at a seam, e.g., via welding. The seam may be located near a node, e.g., at a node or within 10% of the node location. Thereafter, piezoelectric elements 323 of piezoelectric stack 322 may be stacked with first and second electrode assemblies 330 disposed therebetween and positioned to abut proximal face 373b of flared proximal end 373a of proximal body portion 372 of ultrasonic horn 324. Proximal nut 329 may then be positioned to abut the piezoelectric stack 322 and bolt 328 utilized to secure these components to one another under suitable compression, e.g., via extending through proximal nut 329 and piezoelectric stack 322 and engaging aperture 373c of flared proximal end 373a of proximal body portion 372 of ultrasonic horn 324. Electrode assemblies 330 may thereafter or prior thereto be coupled to pass-through electrical contacts 327 of overmold seal 326.

With reference to FIGS. 3 and 5-7, to complete assembly of ultrasonic transducer assembly 320, casing 340 is installed. More specifically, distal body component 344 of body 341 of outer casing 340 is slid over threaded female receiver 325d, extension 325c, and nose 325b of ultrasonic horn 324 and into sealed engagement about and/or in abutment with overmold seal 326. Simultaneously therewith, prior thereto, or thereafter, pass-through electrical contacts 327 are electrically coupled with contact assembly 332. To finish the assembly of casing 340, the one or more proximal body components 342 are slid proximally and joined to one another and/or distal body component 344, e.g., via welding, such that overmold seal 326, casing 340, and ultrasonic horn 324 cooperate to hermetically seal enclosure 345 enclosing internal volume 349 containing the piezoelectric stack 322, a proximal portion of ultrasonic horn 324, bolt 328, proximal nut 329, and first and second electrode assemblies 330 therein (see FIG. 2).

In embodiments, in addition or as an alternative to overmold seal 326, an overmold seal 335 (FIG. 2) may be formed about aperture 334 of distal body component 344 to hermetically seal against nose 325b of ultrasonic horn 324 upon insertion of nose 325b therethrough during assembly. Further still, as an alternative to overmolding overmold seal 335 (FIG. 2) about aperture 334 of distal body component 344, the entire distal body component 344 may be formed from an overmold material that is overmolded to a distal-most of the proximal body components 342 to similarly establish a seal about ultrasonic horn 324. The various components of casing 340 may thus be formed from electrically-conductive material that are welded or otherwise joined, and/or overmold materials; polymeric materials for some or all of casing 340 are also contemplated.

In embodiments, two or more of the above-detailed manufacturing steps may be performed together. For example, in embodiments, distal body portion 374 of ultrasonic horn 324, pass-through contacts 327, and distal body component 344 of outer casing 340 (and, in embodiments, contact assembly 332 also) are inserted into a mold (not shown) and overmold material is injected into the mold in and/or around these components to form overmold seal 326 and seal these components to one another as a single integrated unit.

Referring generally to FIGS. 2-7, the above-detailed sealing of casing 340 about ultrasonic horn 324 to hermetically seal enclosure 345 ensures that transducer assembly 320 is capable of withstanding multiple rounds of sterilization, e.g., autoclave sterilization, without leaking or being damaged.

While several embodiments of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular embodiments. Those skilled in the art will envision other modifications within the scope and spirit of the claims appended hereto.

What is claimed is:

1. An ultrasonic transducer assembly of an ultrasonic surgical instrument, comprising:
   a piezoelectric stack;
   an ultrasonic horn secured to and extending distally from the piezoelectric stack, the ultrasonic horn including a body and a nose extending distally from the body;
   an overmold seal about the body of the ultrasonic horn; and
   a casing disposed about the piezoelectric stack, the body of the ultrasonic horn, and the overmold seal, the casing defining a distal opening through which the nose of the ultrasonic horn extends, the overmold seal establishing a hermetic seal with the casing to define a hermetically sealed interior enclosing the piezoelectric stack and the body of the ultrasonic horn therein, wherein the casing is configured to be arranged in a housing of a surgical instrument, wherein the body of the ultrasonic horn defines at least one radially-facing recess, and wherein the overmold seal is arranged about and within the at least one radially-facing recess and includes at least one pass-through electrical connector extending therethrough.

2. The ultrasonic transducer assembly according to claim 1, wherein the body of the ultrasonic horn includes first and second body portions joined to one another at a seam.

3. The ultrasonic transducer assembly according to claim 2, wherein the first and second body portions are joined to one another at the seam via welding.

4. The ultrasonic transducer assembly according to claim 2, wherein the seam is disposed near a node location along the ultrasonic horn.

5. The ultrasonic transducer assembly according to claim 2, wherein the first and second body portions include complementary opposing faces to facilitate joining.

6. The ultrasonic transducer assembly according to claim 1, wherein the body of the ultrasonic horn defines a plurality of radially-facing recesses.

7. The ultrasonic transducer assembly according to claim 1, wherein the at least one radially-facing recess of the body of the ultrasonic horn is discontinuous.

8. The ultrasonic transducer assembly according to claim 1, further comprising first and second electrode assemblies disposed within the hermetically sealed interior and associated with the piezoelectric stack, the first and second electrode assemblies electrically coupled to first and second pass-through electrical connectors of the at least one pass-through electrical connector.

9. The ultrasonic transducer assembly according to claim 1, wherein the casing includes a plurality of casing components joined to one another at hermetically sealed seams.

10. An ultrasonic surgical instrument, comprising:
    a handle assembly, including:
      a housing; and
      an ultrasonic transducer assembly supported by the housing, including:
        a piezoelectric stack;
        an ultrasonic horn secured to and extending distally from the piezoelectric stack, the ultrasonic horn including a body and a nose extending distally from the body;
        an overmold seal about the body of the ultrasonic horn; and
        a casing disposed about the piezoelectric stack, the body of the ultrasonic horn, and the overmold seal, the casing defining a distal opening through which the nose of the ultrasonic horn extends, the overmold seal establishing a hermetic seal with the casing to define a hermetically sealed interior enclosing the piezoelectric stack and the body of the ultrasonic horn therein, wherein the casing is arranged in the housing of the handle assembly, wherein the body of the ultrasonic horn defines at least one radially-facing recess, and wherein the overmold seal is arranged about and within the at least one radially-facing recess and includes at least one pass-through electrical connector extending therethrough; and an elongated assembly extending distally from the handle assembly, the elongated assembly including a waveguide configured to engage the nose of the ultrasonic horn, the waveguide defining a blade at a distal end thereof, wherein ultrasonic energy produced by the piezoelectric stack is transmitted along the ultrasonic horn and the waveguide to the blade for treating tissue adjacent the blade.

11. The ultrasonic surgical instrument according to claim 10, wherein the body of the ultrasonic horn includes first and second body portions joined to one another at a seam.

12. The ultrasonic surgical instrument according to claim 11, wherein the first and second body portions are joined to one another at the seam via welding.

13. The ultrasonic surgical instrument according to claim 11, wherein the seam is disposed near a node location along the ultrasonic horn.

14. The ultrasonic surgical instrument according to claim 11, wherein the first and second body portions include complementary opposing faces to facilitate joining.

15. The ultrasonic surgical instrument according to claim 10, wherein the body of the ultrasonic horn defines a plurality of radially-facing recesses.

16. The ultrasonic surgical instrument according to claim 10, wherein the at least one radially-facing recess of the body of the ultrasonic horn is discontinuous.

17. The ultrasonic surgical instrument according to claim 10, further comprising first and second electrode assembles disposed within the hermetically sealed interior and associated with the piezoelectric stack, the first and second electrode assemblies electrically coupled to first and second pass-through electrical connectors of the at least one pass-through electrical connector.

18. The ultrasonic surgical instrument according to claim 10, wherein the casing includes a plurality of casing components joined to one another at hermetically sealed seams.

* * * * *